(12) United States Patent
Richter et al.

(10) Patent No.: US 12,245,838 B2
(45) Date of Patent: Mar. 11, 2025

(54) SYSTEM FOR MEASURING CHARGES PROPAGATING THROUGH A BIOLOGICAL OBJECT

(71) Applicants: Wolfgang Richter, Vancouver (CA); Faranak Zadeh, Vancouver (CA)

(72) Inventors: Wolfgang Richter, Vancouver (CA); Faranak Zadeh, Vancouver (CA)

(73) Assignee: EPIC SEMICONDUCTORS INC

( * ) Notice: Subject to any disclaimer, the term of this patent is extended or adjusted under 35 U.S.C. 154(b) by 1035 days.

(21) Appl. No.: 17/067,660

(22) Filed: Oct. 10, 2020

(65) Prior Publication Data

US 2021/0025867 A1    Jan. 28, 2021

Related U.S. Application Data

(63) Continuation-in-part of application No. 16/915,318, filed on Jun. 29, 2020, now abandoned.

(Continued)

(51) Int. Cl.
*A61B 5/00* (2006.01)
*G01N 27/327* (2006.01)
(Continued)

(52) U.S. Cl.
CPC ....... *A61B 5/0028* (2013.01); *G01N 27/3273* (2013.01); *G01N 33/48785* (2013.01); *A61B 5/283* (2021.01); *A61B 2560/0219* (2013.01)

(58) Field of Classification Search
None
See application file for complete search history.

(56) References Cited

U.S. PATENT DOCUMENTS 4,361,153 A * 11/1982 Slocum ............... A61B 5/0031
                                                           128/903
4,528,987 A *  7/1985 Slocum ............... A61B 5/0006
                                                           600/509

(Continued)

OTHER PUBLICATIONS

"Transponder." Merriam-Webster. 2018. https://web.archive.org/web/20181117193146/https://www.merriam-webster.com/dictionary/transponder (Year: 2018).*

*Primary Examiner* — Meredith Weare

(57) ABSTRACT

Disclosed is a system for measuring electrical charges propagating through a biological object. The system includes an implantable medical device inserted into the biological object, an electronic implant attached to the implantable medical device for measuring, processing and communicating electrical charges, at least one transponder configured on the implantable medical device to convert mechanical waves into electrical charges, wherein the electrical charges propagate through the biological object to be received by the electronic implant; and an external electronic hub device for providing electrical charges to influence the biological object. The external electronic hub device includes a controller, a frequency generator, a resonator, a filter unit, and an electrode. The electronic implant includes an arrangement of sub-circuits, an energy convertor, an amplifier, an analog/digital converting logic circuit, and a modulator. The amplifier receives the amplified bio-electrical charges while suppressing electrical influence, further the amplifier creates an amplified analog value representing the bio-electrical charges.

8 Claims, 3 Drawing Sheets

Related U.S. Application Data

(60) Provisional application No. 62/869,183, filed on Jul. 1, 2019.

(51) Int. Cl.
  *G01N 33/487* (2006.01)
  *A61B 5/283* (2021.01)

(56) References Cited

U.S. PATENT DOCUMENTS

| | | | |
|---|---|---|---|
| 2004/0133242 A1* | 7/2004 | Chapman | A61B 5/29 607/5 |
| 2008/0092911 A1* | 4/2008 | Schulman | A61N 1/37288 600/549 |
| 2012/0004523 A1* | 1/2012 | Richter | A61B 5/25 600/509 |
| 2012/0078322 A1* | 3/2012 | Dal Molin | A61B 5/0028 607/32 |
| 2016/0073883 A1* | 3/2016 | Charrat | A61B 5/021 600/300 |
| 2017/0332908 A1* | 11/2017 | Uno | A61B 5/681 |
| 2018/0055386 A1* | 3/2018 | Zielinski | A61B 5/02108 |
| 2018/0164884 A1* | 6/2018 | Richter | G06F 3/015 |
| 2020/0015722 A1* | 1/2020 | Gopinathan | A61B 5/686 |
| 2020/0337563 A1* | 10/2020 | Andersen | A61B 5/0031 |
| 2021/0000348 A1* | 1/2021 | Richter | A61B 5/6833 |

\* cited by examiner

SYSTEM FOR MEASURING CHARGES PROPAGATING THROUGH A BIOLOGICAL OBJECT

CROSS REFERENCE TO RELATED APPLICATION

The present application is a continuation-in-part of U.S. patent application Ser. No. 16/915,318, entitled "AN APPARATUS FOR MEASURING VITAL SIGNS," filed on Jun. 29, 2020, further the U.S. patent application Ser. No. 16/915,318 claims the benefit of U.S. Provisional Application No. 62/869,183, filed Jul. 1, 2019, which are incorporated by reference in their entirety.

BACKGROUND OF THE INVENTION

1. Field of the Invention

The present invention generally relates to an implantable medical device, and more particularly relates to a system for measuring electrical charges propagating through a biological object.

2. Description of Related Art

To measure vital signs of biological objects (like humans) the art knows about electronic devices which are external attached directly to the object via electrodes or sensing elements e.g. for pressure or sound. The object's metabolism creates specific signals which are electrical, mechanical, and acoustical.

For measurement of the object's health status, or if its organs are fully functional, samples might have to be extracted and analyzed. Sometimes, the object is exposed to radiation (e.g. X-ray, MRI, cobalt, etc.) to create an image of its inner constitution. The disadvantage of such procedures is their sumptuous efforts or momentarily results which do not reflect the real condition of the object.

Wearable computing in the form of e.g. smartwatches measure at least the most significant vital signs like pulse, or the object's temperature, which may not be the cause of or reflect health problems. Exploding costs are a burden for every healthcare system, while it seems apparent that early detection of diseases is better for the system and for curing the object, rather than to fight long-term suffering.

A majority of health problems are related to blood circulation and the heart itself. False nutrition or lifestyle can cause clogs in the arteries which can lead to strokes or heart attacks in the long term. Once diagnosed, clogged arteries must be freed with surgical measures e.g. by the use of catheters and stents. Detecting clogs goes along with extensive measures like unpleasant injection of contrast liquid, X-ray, malaise, etc.

Implants can stabilize a biological object or enhance its features. While mechanical implants (often uncontrolled) support the skeleton, electronic implants can check such for proper function or monitor or stimulate muscles, organs (e.g. heart) and the brain, as well as their interconnections.

However, most of the implants are not useful during (or support) the implantation process or not able to deliver continuous versatile vital signs monitoring due to their power restrictions. Therefore, there is a need for a system for using and measuring electrical charges propagating through a biological object. Further, the system should be able to assist in detecting (and measuring) clogs in blood vessels during the implantation process, vital signs or diseases.

SUMMARY OF THE INVENTION

In accordance with teachings of the present invention, a system for measuring charges propagating through a biological object is provided.

An object of the present invention is to provide the system with an implantable medical device inserted into the biological object, an electronic implant attached to the implantable medical device for measuring, processing and communicating electrical charges, at least one transponder configured on the implantable medical device to convert mechanical waves into electrical charges, wherein the electrical charges propagate through the biological object to be received by the electronic implant; and an external electronic hub device for providing electrical charges to influence the biological object.

The external hub device includes a controller contactlessly power and communicates data with the electronic implant, a frequency generator for generating alternating charges, a resonator for resonating and reflecting data modulation, a filter unit for mixing data received from the controller with the alternating charges and further the filter unit filters and directs data from the electronic implant to the controller; and an electrode for emitting the alternating charges as alternating electric field influencing the biological object and the electronic implant.

The electronic implant includes an arrangement of sub-circuits, an energy convertor for harvesting and rectifying alternating electric field from the biological object, further the energy convertor provides a DC energy, stores the DC energy and provides differential voltages, an amplifier for amplifying amplitude of received bio-electrical charges from the biological object, an analog/digital converting logic circuit for generating digitized information from the received amplified bio-electrical charges values from the amplifier; and a modulator to modulate digitized information with external provided alternating electric field to be received from the external electronic hub. The amplifier receives the amplified bio-electrical charges to suppress electrical influence, further the amplifier creates an amplified analog value representing the bio-electrical charges.

Another object of the present invention is to provide the external hub device with a bi-directional communication unit coupled to the controller to communicate the data over a communication network. Further, the electronic implant includes a dynamic sequencer for storing a sequencing information received from the external electronic hub device.

Another object of the present invention is to provide the electronic implant with an array of smart switches to temporarily power and connect the electronic sub-circuits of the electronic implant to the modulator or other sub-circuits under the control of dynamic sequencer. The electronic implant detects clogging in arteries and further propagates the electric charges caused due to clogging over the biological object.

Another object of the present invention is to provide the electronic implant having a first Schmitt trigger generates a master clock from the alternating charges, a second Schmitt trigger, a data separator puts a sequence into the dynamic sequencer, a first gate to link the master clock from the second Schmitt trigger on receiving signal from the first Schmitt trigger, a shift register counts the number of clocks during the time the second Schmitt trigger is triggered, a counter derives a carrier frequency from the master clock, a second gate mixes and modulates the alternating electric field with the data from the shift register, a hardware interpreter interprets the data in the dynamic sequencer; and an electrode releases the impedance.

Another object of the present invention is to provide the smart switch with a first transmission gate powers the selected electronic sub-circuit on receiving enable signals from the dynamic sequencer; a buffer for storing generated electrical charges; a second transmission gate links the electric charges to the buffer; a comparator monitors the selected sub-circuit, further the comparator triggers an output if the sub-circuits is ready to operate; and a third transmission gate links the charge from the buffer to the selected sub-circuit on receiving command from the comparator and the dynamic sequencer, wherein the comparator switches off.

To the accomplishment of the foregoing and related ends, the one or more embodiments comprise the features hereinafter fully described and particularly pointed out in the claims. The following description and the annexed drawings set forth in detail certain illustrative aspects of the one or more embodiments. These aspects are indicative, however, of but a few of the various ways in which the principles of various embodiments may be employed and the described embodiments are intended to include all such aspects and their equivalents.

DETAILED DESCRIPTION OF DRAWINGS

Figure 1:
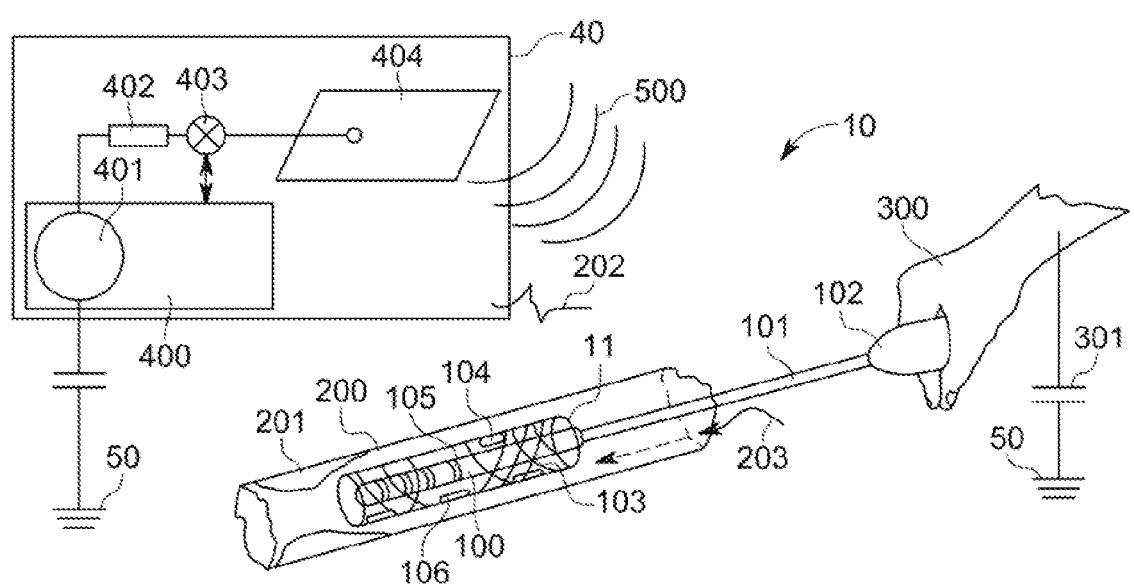
FIG. 1 illustrates a schematic diagram of an implantable system for measuring electrical charges propagating through a biological object.

Various embodiments are now described with reference to the drawings, wherein like reference numerals are used to refer to like elements throughout. In the following description, for purposes of explanation, numerous specific details are set forth in order to provide a thorough understanding of one or more embodiments. It may be evident, however, that such embodiment(s) may be practiced without these specific details. In other instances, well-known structures and devices are shown in block diagram form in order to facilitate describing one or more embodiments.

FIG. 1 illustrates a schematic diagram of a system 10 for measuring electrical charges propagating through a biological object 200. The system 10 includes an implantable medical device 100, an electronic implant 104, at least one transponder 105 and an external electronic hub device 40. The implantable medical device 100 is inserted into the biological object 200. The electronic implant 104 is attached to the implantable medical device 100 for measuring, processing and communicating electrical charges. The electronic implant 104 is explained in detail in conjunction with FIG. 3 of the present invention.

The transponder 105 is configured on the implantable medical device 100 to convert mechanical waves into electrical charges. Alternatively, in another embodiment, the implantable medical device 100 acts as a transponder. The electrical charges propagate through the biological object 200 to be received by the electronic implant 104. Examples of the transponder 105 include but not limited to piezo rings, electrodynamic magnetic or capacitive converters, MEMS, etc.

The external electronic hub device 40 provides electrical charges to influence the biological object 200. The external electronic hub device 40 includes a controller 400, a frequency generator 401, a resonator 402, a filter unit 403, and an electrode 404. The controller 400 contactlessly powers and communicates data with the electronic implant 104 by emitting alternating electric charges by the electrode 404. The controller 400 is able to generate frequency either with the frequency generator 401 or as per with software algorithm.

The frequency generator 401 generates alternating electric charges. The resonator 402 resonates and reflects data modulation. The filter unit 403 mixes data received from the controller 400 with the alternating charges. Further, the filter unit 403 filters and directs data from the electronic implant 104 to the controller 400. The electrode 404 emits the alternating charges as an alternating electric field, influencing the biological object 200 and the electronic implant 104.

The resonator 402 resonates the frequency to a higher amplitude level (e.g. 200 eV) and reduces the electrical current of the resulting wave (e.g. 200 uA). The filter unit 403 allows to (de-)modulate data, using the frequency as a carrier. The frequency emits from the electrode 404 as an alternating electric field 500, which influences the biological object 200, and therefore the electronic circuitry 104 in the form of alternating electric charges.

These charges propagate further through the biological object 200 and the conductive liquid of the flexible tube 101, the pump 102, and the surgeon 300 couples capacitively 301 into the earth's ground 50. The external controller 400 couples to the earth's ground 50 as well, which creates a closed electrical circuit.

The electronic implant 104 harvests electrical energy from the charges of the alternating electric field 500 and converts the field's frequency into a system clock to operate its sub-circuits. The electronic implant 104 then receives electrical charges provided by the biological object 200, which propagate through the object's 200 body, e.g. the electrical signal from the heart (ECG) 202. The heart pumps blood through the artery 200 in form of a pulse wave 203 where the balloon or catheter 11 is inserted. The electronic implant 104 is bioresorbable.

As the electrical signal 202 from the heart propagates quicker than the biomechanical pulse waves 203, both signals pass the electronic implant 104 at different time intervals 204. The transponder 105 is attached to the balloon or on transponder areas 106 on a stent 103.

The transponder 105 converts the biomechanical pulse wave into electric charges, which the electronic implant 104 receives, samples, digitizes and modulates as data into the external provided alternating electric field 500. This creates a change on the impedance of the resonator 402 which the filter mixer 403 demodulates and further conducts to the controller 400. The controller 400 has means and algorithms to analyze the data or to communicate over networks.

Once the in the biological object's artery 200 inserted balloon 11/stent 103 reaches a clog 201, the amplitude and speed of the pulse wave changes (due to the Bernoulli effect)

which the external controller 400 signalizes to the surgeon 300, who then expands the balloon to widen the artery 200 and/or place the stent 103.

Alternatively, the electronic implant 104 includes an electromagnetic wave unit (not shown in FIGURES) for releasing situation related output signals. Examples of the output signals include but not limited light signals, radio-waves, radio-pulses etc. The output signals are recognizable by the surgeon. Examples of the electromagnetic wave unit include but not limited to LED's, RF transmitters, OLED, oscillators etc.

For exemplary purposes, the electromagnetic wave unit emits optical signals for the surgeon, utilizing the tube 101 as a kind of light pipe. The electromagnetic wave unit releases optical signals when the catheter 11 passes through the clog 201 area in the artery 200. The output signals are released based on the identified change in the transponded electrical charges caused due to clogging the pulse wave 203. The tube 101 may also be used as an antenna for emitting radio-wave signals.

Examples of the controller 400 include but not limited to MCU, FPGA, PLC, etc. Examples of the frequency generator 401 include but not limited to oscillators, PWM, resonators, etc. Examples of the resonator 402 include but not limited to coil, transformer, gyrator etc. Examples of the filter unit 403 include but not limited to passive/active low/high/band pass, mixer, amplifier, PLL, etc.

In an embodiment of the present invention, the implantable medical device 100 is a catheter. The catheter 11 consists of a balloon extending from a flexible tube 101 which contains a (preferable) conductive liquid (e.g. salted water). The catheter 11 further includes a pump 102 used to expand a balloon under the control of a surgeon/doctor 300.

The catheter 11 carries a stent 103 with the purpose to widen the biological object 200 (hereinafter also termed as artery 200) at the position of a clog 201. The electronic implant 104 may be attached to the stent 103 or to the balloon (dielectric). The stent 103 may also act as an electrode. Alternatively, though not shown in FIGURES, due to conductivity (e.g. of the liquid in the tube 101), the electronic implant 104 may further be attached to the pump 102. The electronic implant 104 detects clogging in arteries 200 and further propagates the electric charges caused due to clogging over the biological object 200.

Figure 2:
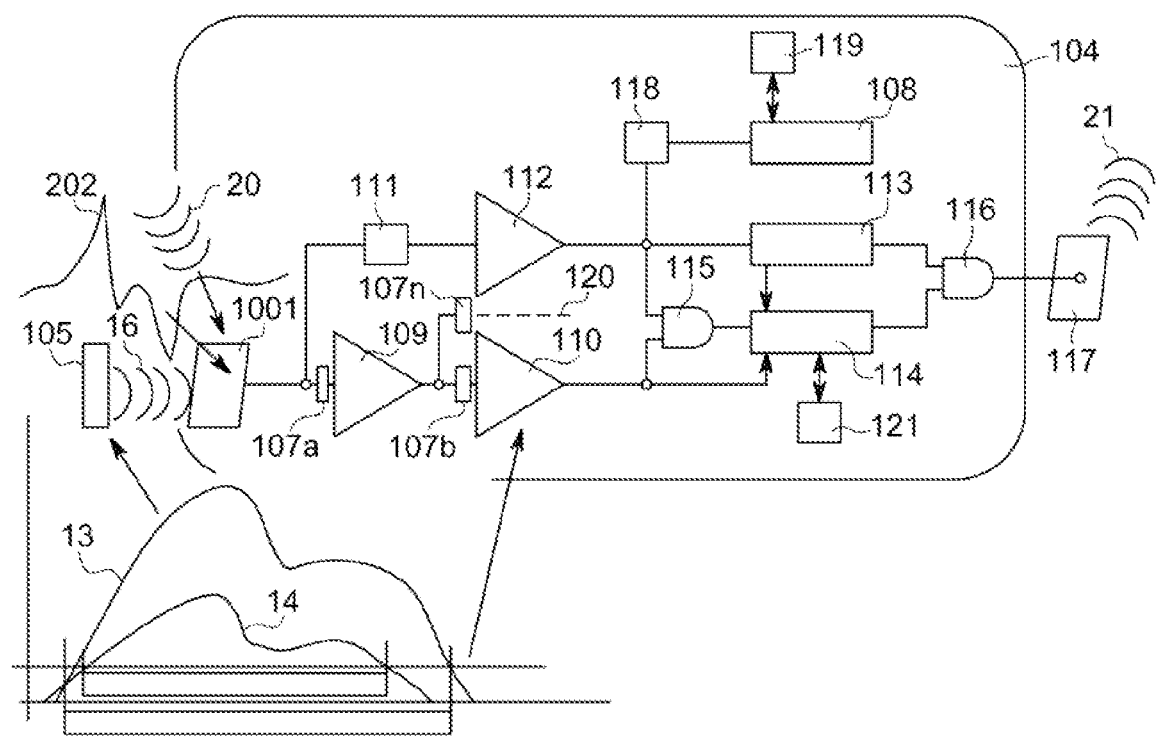
FIG. 2 illustrates a schematic diagram of an electronic implant interacting with and transponding mechanical waves initiated from the biological object, and how internal and external electrical charges are received and processed.

FIG. 2 illustrates a schematic diagram of an electronic implant 104 interacting with bioelectrical and mechanical waves initiated from the biological object 200. The electronic implant 104 includes an arrangement of sub-circuits (600, shown in FIG. 3), an energy convertor 111, an amplifier 109, an analog/digital converting logic circuit 110, and a modulator 116.

The energy convertor 111 harvests and rectifies the external provided alternating electric field 20 influencing the biological object (200, shown in FIG. 1). The energy convertor 111 provides DC energy, stores the DC energy and provides differential voltages. Examples of the energy convertor 111 include but not limited to diode rectifiers, Graetz bridge, AC/DC convertors, MOS switches etc.

The amplifier 109 amplifies the amplitude of received bio-electrical charges 202 from the biological object (200, shown in FIG. 1). The amplifier 109 receives the amplified bio-electrical charges 202 while suppressing disturbing electrical influence. The amplifier 109 creates an amplified analog value representing the bio-electrical charges. Examples of the amplifier 109 include but not limited to instrumentation amplifier, programmable amplifier, differential OPs, etc.

The analog/digital converting logic circuit 110 generates digitized information from the received amplified bio-electrical charges values from the amplifier 109. The modulator 116 modulates the digitized information with the external provided alternating electric field 21 via a conductive surface 117 of the implant, acting as an electrode, to be received from the external electronic hub device 40.

In another embodiment of the present invention, the electronic implant 104 further includes a first (comparator) Schmitt trigger 112, a data separator 118, a dynamic sequencer 108, a first gate 115, a shift register 114, a counter 113, a hardware interpreter 119, and an electrode 117. Herein the modulator 116 is working as a second (AND) gate, and hereinafter the modulator 116 is alternatively written as second AND gate 116.

The electronic implant 104 has a transponder electrode 1001 (which may be e.g. the metallic stent 103 of the catheter 11, shown in FIG. 1), a printed conductive structure on the balloon (similar to catheter 11, shown in FIG. 1) or alternatively on the organic tissue of the biologic object 200. The electronic implant 104 further includes an array of smart switches 107*a,b . . . n*, to temporarily power and connect the electronic sub-circuits (600 shown in FIG. 3) to the modulator 116 or other sub-circuits under the control of the dynamic sequencer 108.

The electronic implant 104 is influenced by electric charges 20, propagating through the biological object 200 (human, animal, plant) when inserted inside the biological object 200. An external provided alternating electric field 20 influences the transponder electrode 1001, that connects the resulting electrical charges to an energy convertor 111 which rectifies and buffers usable DC power from the electrical charges.

The first Schmitt Trigger 112 generates the system master clock from the received alternating charges 20 for the implant's electronic circuitry. The alternating electric field 20 is modulated (external & internal) with data. The data separator 118 demodulates and loads a received data sequence into the dynamic sequencer 108. Further, the data separator 118 stores sequence information received from the external electronic hub device 40.

The hardware interpreter 119 interprets the data in the dynamic sequencer 108 stepwise as commands or for selecting the smart switches 107*a,b,c, . . . n* to activate other sub-circuits 120. For example, the smart switch 107*a* is selected, a charge (also known as instrumentation-) amplifier is connected to the electrode 1001 to receive e.g. an ECG signal 202 from the biological object (200, shown in FIG. 2).

The resulting pulse wave 13 propagates as compressed bloodstream through the specific artery, yet changes by increasing speed and reduced amplitude 14 when passing a clogged part of the blood vessel. The transponder 105 (e.g. a piezo ring, pressure sensitive polymers, etc.) creates a voltage pulse 16 analog to the pulse wave which also propagates through the medium and influences electrode 1001, passes the smart switch 107*a*, and gets amplified by the charge/instrumentation amplifier 109.

The amplifier 109 output is connected to the analog/digital converting logic circuit 110 which integrates the pulse to a time length signal that opens the first AND gate 115 to link the master clock from the first Schmitt Trigger 112 to the counter/shift register 114 that counts the number of clocks during the time the analog/digital converting logic circuit 110 is triggered, otherwise it resets.

The number of counted clocks represents the presence of a clog in the artery, as well as its dimensions (the invention related implant 104 also sends a beacon signal (not shown in FIGURES) to determine its position in the biological object by an external device). The counter 113 derives a carrier frequency, a beacon frequency, a timeslot, and a shift clock from the master clock.

At a certain time slot the second AND gate 116 acts as a mixer and modulates the alternating electric field 20 with the carrier and the data from the counter/shift register 114 by changing the implants internal and external (of the processor (FIG. 1, not shown in FIG. 2) generating e-field 20) impedance of the field by adding or subtracting modulated electric charges via the electrode 117.

In another embodiment of the present invention, the system (10, shown in FIG. 1) further includes a bi-directional communication unit (not shown in FIGURES) coupled to the controller to communicate the data over a communication network. Examples of the bi-directional communication unit include but not limited to LTE, Wi-Fi, internet, Bluetooth, LAN, GSM, CDMA, and other similar communication networks etc. Further, the implant 104 includes a converter block 121 (e.g. ADC, DAC, PWM etc.) for performing analog digital conversation and vice versa from and to the counter/shift register 114.

Figure 3:
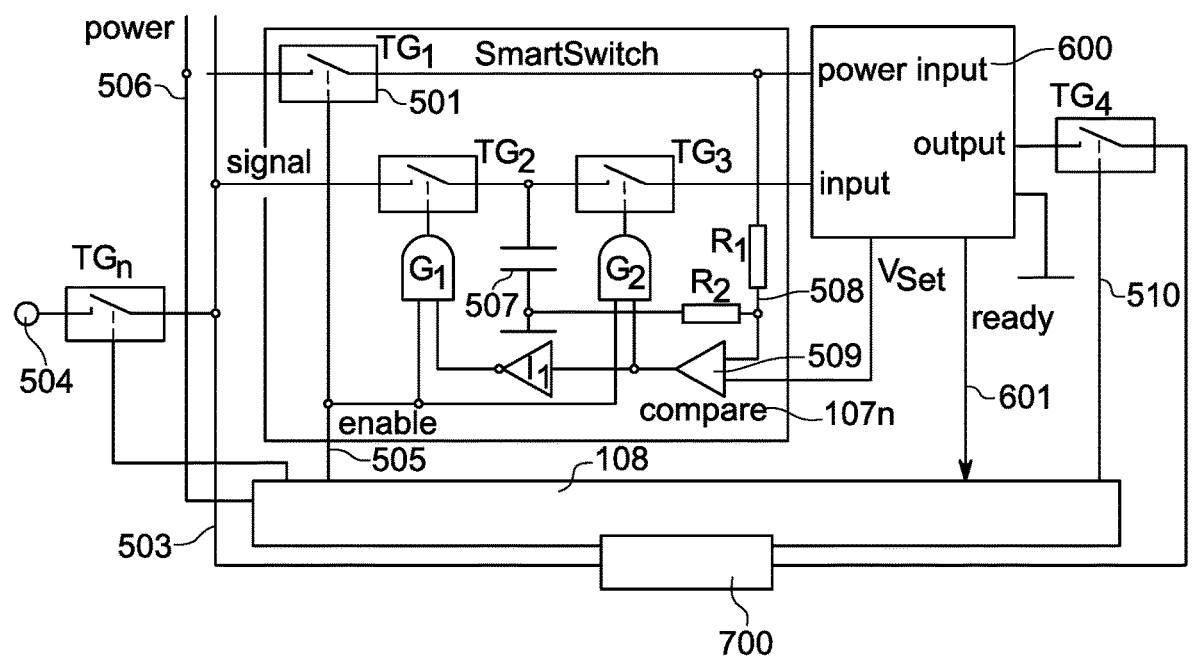
FIG. 3 illustrates a schematic diagram of a variation of a smart switch block in combination with a dynamic sequencer.

FIG. 3 illustrates a schematic diagram of a variation of a smart switch block 107a in combination with a dynamic sequencer 108. The smart switch block 107a includes a first transmission gate 501, a buffer 507, a second transmission gate TG2, a comparator 509, and a third transmission gate TG3.

The first transmission gate 501 powers the selected electronic sub-circuit 600 on receiving enable signals from the dynamic sequencer 108. The buffer 507 stores generated electrical charges. The electrical charges are generated from either the biological object or the other integrated sub-circuits.

The second transmission gate TG2 links the electrical charges to the buffer 507. The comparator 509 monitors the selected sub-circuit. The comparator 509 triggers an output if the sub-circuit is ready to operate. The third transmission gate TG3 links the charge from the comparator 509 and the dynamic sequencer 108. The comparator 509 switches off TG2.

In another embodiment of the present invention, the system 10 further includes a fourth transmission gate TG4 for linking the processed output value of the selected sub-circuit to other sub-circuits on receiving command under command line 510 from the dynamic sequencer 108.

To achieve a versatile modular concept, the invention related electronic implant (104, shown in FIG. 1 and FIG. 2) consists of a variety of digital and analog function block, called as sub-circuits 600. The dynamic sequencer 108 combine them in infinite variations by connecting electrical signals or levels to and from the sub-circuits 600, utilizing the smart switch 107a built from transmission and logic gates.

It would be readily apparent to those skilled in the art that any of the smart switch (107a, 107b . . . 107n) may be utilized by the dynamic sequencer 108 without deviating from the scope of the present invention. In a first step of sequence, the dynamic sequencer 108 inputs a signal from a terminal 504 by activating a transmission gate TGn, which is connected to a signal line 503. The system (10, shown in FIG. 1) also includes a power line 506.

The dynamic sequencer 108 selects a sub-circuit 600 to process the signal by activating a related smart switch 107a (in the exemplary embodiment as shown in FIG. 3) via an "enable" output 505. This activates the switch TG1 which connects electrical power from the power line 506 to the sub-circuit 600. The switch TG2 connects the signal to a sample and hold circuit 507.

After a settling time the sub-circuit 600 is operable and provides this state as a voltage on its output Vset. The comparator 509 compares the voltage level of the sub-circuit 600 with a voltage level provided from a voltage divider 508 (derived from the power line 506). On a match, the comparator 509 deactivates the AND gate G1 (which opens TG2) and closes gate G2 to activate switch TG3, which connects the stored signal to the input of the sub-circuit 600.

After a propagation delay, the sub-circuit 600 provides the result of the signal manipulation on its output and sends a "ready" signal via the signal line 601 to the dynamic sequencer 108 to launch the next step. The dynamic sequencer 108 enables (enable line 510) switch TG4 to connect the power signal with other sub-circuits or outputs through a signal conditioner 700 (=technically another sub-circuit, e.g. buffer, filter, sample and hold attenuator, resonator, doubler, VCO, etc.). This step also disables the smart switch 107a, which removes the power from the sub-circuit 600 for efficiency.

A typical sub-circuit 600, which the dynamic sequencer 108 selects in a kind of round robin sequencer are: Digital sub-circuits like logic gates, flip-flops, (de-) multiplexers, ADC, DAC, PLL, perceptrons, MAC, ALU, adder, ICU, PLC, memory etc. Analog sub-circuits like ((non-)inverting, summing-, instrumentation-) operation amplifiers, filters, multipliers, analog computation, oscillators, attenuators, buffer, filter, S&H, CCD, terminator, resistor, capacitor, inductor, gyrator, (ideal) diodes, transistors, ionizer, etc. Optoelectronic sub-circuits like (UV, IR, RGB) LEDs, photocells (-diodes, -resistors), opto couplers, drivers, camera, arrays, etc. MEMS like accelerometer, gyro, DLP, sound, pressure, micro fluidic structures etc.

The present invention offers various advantages such as an electronically enhanced implant with remotely configurable- and communication features to contactlessly monitor a number of—if not all—vital signs from a biological object. This may be used to inform the object (or caretakers) or to invoke biofeedback, as well as to allow a real-time morale and wellbeing assessment of the object, or provide relief from medical disorders. The electronic implant also increases the biological object's wellbeing and may even provide extra (artificial) senses (e.g. cyborg functions).

The present invention contributes to the modern aspect of telemedicine and monitoring of mobile biological objects. The present invention not only focus on human beings but also concerns pets, livestock, and even (food-) plants. An invention-related bioelectrical "laboratory-on-chip-implant" is sensitive to electrical charges which propagate through the object. Due to the electrical conductivity of the object, the charges may be received at any point of the object's body (yet preferably where they get least attenuated) from the invention's adaptive electronic circuitry.

Typical processing includes but not limited to amplifying, filtering, converting, classifying, calculating, data transmitting/receiving, stimulating, ionizing, shielding, connecting, etc. Therefore, one of the digital function blocks is a sequencer, which may connect or route a selection of the sub-circuits in a specific order to perform a desired processing.

The respective sub-circuit array components (electronic function blocks) may scan a selectable charge pattern of the object (e.g. electrocardiogram ECG, pulse wave etc.) and modulate the external provided alternating charges with the scanning results for further external processing, e.g. form a computing device. The implant may be attached to a supportive carrier, which i.e. may convert mechanical vital signs of the object (e.g. pulse waves or blood pressure) into propagating electrical charges, the implant can receive and process.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. A system for measuring charges propagating through a biological object, the system comprising:
    an implantable medical device adapted to be inserted into the biological object;
    an electronic implant adapted to be attached to the implantable medical device, wherein the electronic implant measures, processes and communicates electrical charges;
    at least one transponder configured on the implantable medical device, wherein the transponder is configured to convert mechanical waves propagating through the biological object into bio-electrical charges, and output the bio-electrical charges such that the bio-electrical charges propagate through the biological object to be received by the electronic implant; and
    an external electronic hub device configured to provide electrical charges to propagate through the biological object, the external hub device comprising:
        a controller configured to contactlessly power the electronic implant, and communicate data with the electronic implant;
        a frequency generator configured to generate alternating charges;
        a resonator configured to resonate and receive modulated data from the electronic implant, the modulated data representing digitized information;
        a filter unit configured to mix data received from the controller with the alternating charges, and filter and direct data from the electronic implant to the controller; and
        an electrode configured to emit the alternating charges as an alternating electric field that propagates through the biological object and influences the electronic implant;
    wherein the electronic implant comprises an arrangement of sub-circuits comprising:
        an electrode configured to receive the alternating electric field emitted by the external electronic hub device and propagating through the biological object, and to receive bio-electrical charges propagating through the biological object, including the bio-electrical charges output by the transponder;
        an energy convertor configured to harvest and rectify the received alternating electric field to provide a DC energy, store the DC energy and provide differential voltages;
        an amplifier configured to amplify the received bio-electrical charges while suppressing electrical influence of the alternating electric field, and create an amplified analog value representing the received bio-electrical charges;
        an analog/digital converting logic circuit configured to generate digitized information from the amplified analog value; and
        a modulator configured to generate modulated data to be received by the electronic hub device by modulating the alternating electric field received from the electronic hub device with the digitized information.

2. The system according to claim 1 wherein the external hub device further comprises a bi-directional communication unit adapted to be coupled to the controller to communicate the data over a communication network.

3. The system according to claim 1, wherein the transponder comprises a pressure sensitive piezo ring to convert mechanical waves propagating through the biological object into bio-electrical charges.

4. The system according to claim 1, wherein the implantable medical device acts as a transponder to convert mechanical waves propagating through the biological object into bio-electrical charges.

5. The system according to claim 1 wherein the electronic implant is bioresorbable.

6. The system according to claim 1, wherein the electronic implant further comprises:
    a first Schmitt trigger configured to generate a master clock from the alternating charges;
    a first gate configured to link the master clock from the first Schmitt trigger on receiving a time length signal representing a pulse wave from the analog/digital converting logic circuit;
    a shift register configured to count a number of master clocks during the time the analog/digital converting logic circuit is triggered, wherein the number of counted clocks determines presence of a clog in an artery;
    a counter configured to derive a carrier frequency from the master clock along with a shift clock, wherein the modulator is further configured to mix and modulate the carrier frequency with the number of counted clocks from the shift register; and
    an electrode configured to connect with the modulator to add or subtract the bio-electrical charges as the digitized information as changes of the impedance of the electronic implant with the modulator as modulation of the alternating electric field to be received by the external hub device.

7. The system according to claim 1, wherein the electronic implant further comprises an electromagnetic wave unit configured to release output signals.

8. The system according to claim 7, wherein the electromagnetic wave unit releases output signals based on identified changes in the transponded bio-electrical charges.

* * * * *